United States Patent [19]

Annoura et al.

[11] Patent Number: 5,621,099

[45] Date of Patent: Apr. 15, 1997

[54] SYNTHETIC METHOD OF HYMENIALDISINE AND ITS DERIVATIVES AND THEIR SYNTHETIC INTERMEDIATES, AND THOSE SYNTHETIC INTERMEDIATES

[75] Inventors: Hirokazu Annoura, Nagaokakyo; Toshio Tatsuoka, Nishinomiya, both of Japan

[73] Assignee: Suntory Limited, Osaka, Japan

[21] Appl. No.: 586,638

[22] PCT Filed: May 17, 1995

[86] PCT No.: PCT/JP95/00941

§ 371 Date: Jan. 18, 1996

§ 102(e) Date: Jan. 18, 1996

[87] PCT Pub. No.: WO95/31462

PCT Pub. Date: Nov. 23, 1995

[30] Foreign Application Priority Data

May 18, 1994 [JP] Japan ................................... 6-104030

[51] Int. Cl.[6] .............................................. C07D 487/04
[52] U.S. Cl. ............................................................ 540/521
[58] Field of Search .................................................. 540/521

[56] References Cited

U.S. PATENT DOCUMENTS 5,206,239 4/1993 Mizuno et al. ...................... 540/521

FOREIGN PATENT DOCUMENTS

93/16703 9/1993 WIPO ................................. 540/521

OTHER PUBLICATIONS

Annoura et al, "Total Syntheses of Hymenialdisine and Debromohymenialdisine: Stereospecifc Construction of the 2-Amino-4-Oxo-2-Imidazolin-5(Z)-Disubstituted Ylidene Ring System", *Tetrahedron Letters*, 36(3):413–416 (1995).

Cimino et al, "Isolation and X-ray Crystal Structure of A Novel Bromo-Compound from Two Marine Sponges", *Tetrahedron Letters*, 23(7):767–768 (1982).

Endo et al, "Pharmacologically Active Substances from Southern Pacific Marine Invertebrates", *Pure & Appl. Chem.*, 58(3):387–394 (1986).

Kitagawa et al, "Marine Natural Products. XII.[1]) On the Chemical Constituents of the Okinawan Marine Sponge *Hymeniacidon aldis*", *Chem. Pharm. Bull.*, 31(7):2321–2328 (1983).

Kobayashi et al, "α-Adrenoceptor Blocking Action of Hymenin, a Novel Marine Alkaloid", *Experientia* 44, 86–87 (1988).

Y. Nishizuka, "The Family of Protein Kinase C for Signal Transduction", *JAMA*, 262(13):1826–1833 (1989).

Y. Nishizuka, "The Molecular Heterogeneity of Protein Kinase C and its Implications for Cellular Regulation", *Nature*, 334(25):661–665 (1988).

Pettit et al, "Antineoplastic Agents. 168. Isolation and Structure of Axinohydantoin[1]", *Can. J. Chem.*, 68:1621–1624 (1990).

Prager et al, "Knoevenagel Reactions of 6,7–Dihydro–pyrrolo[2,3–c]azepine–4,8(1H,5H)–dione: An Approach to the Synthesis of Pyrrolic Marine Natural Products", *Aust. J. Chem.*, 45:1771–1777 (1992).

Prager et al, "Approaches to the Synthesis of 5–Benzylidene–2–imidazolin–4–ones", *Aust. J. Chem.*, 43:367–374 (1990).

Schmitz et al, "Marine Natural Products: Pyrrololactams from Several Sponges", *Journal of Natural Products*, 48(1):47–53 (1985).

Sharma et al, "Characterizatioin of a Yellow Compound Isolated from the Marine Sponge *Phakellia flabellata*", *J.C.S. Chem. Comm.*, 435–436 (1980).

Primary Examiner—Robert T. Bond
Attorney, Agent, or Firm—Burns, Doane, Swecker & Mathis, L.L.P.

[57] ABSTRACT

The present invention provides hymenialdisine or its derivatives having the formula (I):

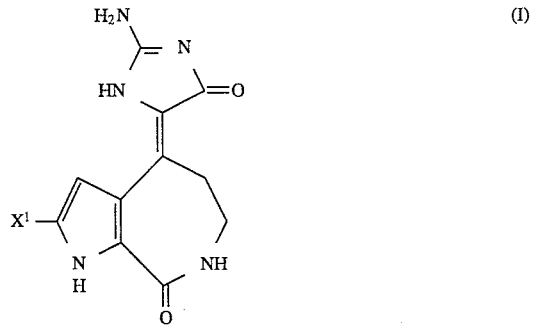

wherein $X^1$ is a halogen atom or a hydrogen atom and a process for production of the same. Further, synthetic intermediates are included in the invention. Hymenialdisine and its derivatives have inhibitory effects against protein kinase C and can be expected to have applications as a drug for the treatment of conditions where it is believed the activation of protein kinase C is involved.

5 Claims, No Drawings

SYNTHETIC METHOD OF HYMENIALDISINE AND ITS DERIVATIVES AND THEIR SYNTHETIC INTERMEDIATES, AND THOSE SYNTHETIC INTERMEDIATES

TECHNICAL FIELD

The present invention relates to a process of producing of hymenialdisine, its derivatives, and their salts of the formula (I):

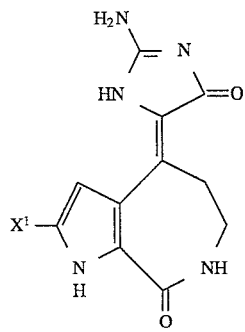

(wherein $X^1$ is a halogen atom or hydrogen atom.) The present invention further relates to intermediates for producing the above compound (I) and processes for producing the same.

BACKGROUND ART

In recent years, there have been intense exploration and study of bioactive substances derived from the sea. Among these, useful substances holding forth promise as pharmaceuticals and lead compounds for pharmaceuticals have been discovered. For example, hymenialdisine and debromohymenialdisine have been isolated from sponges.

For example, hymenialdisine has been isolated from *Axinella verrucosa, Acanthella aurantiaca* (Cimino, G. et al: Tetrahedron Lett., 23, 767 (1982)), *Hymeniacidon aldis* (Kitagawa, I. et al: Chem. Pharm. Bull., 31, 2321 (1983)), and an unconfirmed *Kololevu sponge* (Schmitz, F. et al: J. Nat. Prod., 48, 47 (1985)), while debromohymenialdisine has been isolated from *Phakellia flabellata* (Sharma, G. et al: J. Chem. Soc., Chem. Commun., 435 (1980)) and *Hymeniacidon aldis* (Kitagawa, I. et al: Chem. Pharm. Bull., 31, 2321 (1983); Endo, M. et al: Pure & Appl. Chem., 58, 387 (1986)).

In the above formula (I), the compound having an $X^1$ of a bromine atom is hymenialdisine, while the compound having an $X^1$ of a hydrogen atom is debromohymenialdisine. These compounds have interesting biological activities.

Hymenialdisine and debromohymenialdisine are known to have antineoplastic activities (Pettit, G. et al: Can. J. Chem., 68, 1621 (1990)). Furthermore, debromohymenialdisine is known to have α-adrenoceptor blocking effect (Kobayashi, J. et al: Experimentia., 44, 86 (1988)).

Recently, it has been shown that hymenialdisine and debromohymenialdisine have an inhibitory action against protein phosphokinases, in particular, protein kinase C (Nishizuka, Y.: Nature, 334, 661 (1988); idem, JAMA, 262, 1826 (1989)), which plays an important role in cellular signal transduction (Nambi, P. et al: International Disclosure WO93/16703). They are expected to have applications as drugs for the alleviation and treatment of conditions believed to involve the activation of protein kinase C, for example, cerebral ischemic disorders, cerebral vasospasm, ischemic cardiac diseases, high blood pressure, arteriosclerosis, inflammation, asthma, kidney disorders, rheumatoid arthritus, and sthenia of immunofunctions.

Hymenialdisine and debromohymenialdisine, however, can only be obtained in minute quantities when extracted and isolated from nature, so there has been a strong demand for the development of an efficient process of production enabling economical mass production of hymenialdisine and its derivatives. Such a technique, however, has not yet been known. There has just been a few studies on conversion from aldisin. Even these have not given satisfactory results. Complete synthesis is not yet achieved (Prager, R. et al: Aust. J. Chem., 43, 367 (1990); idem, ibid. 45, 1771 (1992)).

DISCLOSURE OF THE INVENTION

In view of the above situation, the objective of the present invention is to provide a process for economically and efficiently producing of hymenialdisine and its derivatives at a mass production.

The other objectives of the present invention are to provide synthetic intermediates useful for the production of these compounds and a process for producting the same.

The present inventors succeeded in the complete chemical synthesis of hymenialdisine and its derivatives having the formula (I):

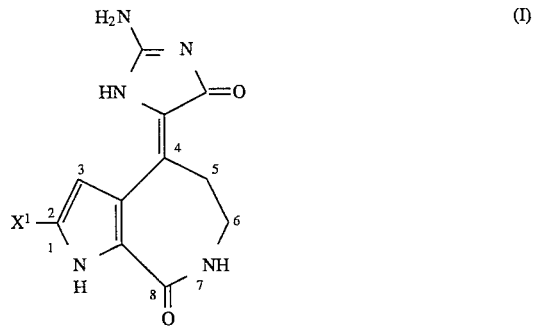

(wherein $X^1$ is a halogen atom or hydrogen atom.)

BEST MODE FOR CARRYING OUT THE INVENTION

It should be noted that natural substances such as hymenialdisine have Z-configuration at the double bond of the 4-position of the pyrrolo[2,3-c]azepine skeleton. However, according to the present invention, the resultant hymenialdisine and its derivatives are surprisingly obtained only in the z-configuration form. The halogen atom referred to in the present invention includes a chlorine atom, bromine atom, and iodine atom.

The hymenialdisine having the formula (I) and its derivatives can be synthesized by the processes shown below. These processes will be explained one after the other.

First, in the following process steps 1 and 2, the compounds (IIa) and (IIb) are obtained from the known starting materials (VIII) and (XV), then the compound (IV) is obtained from these compounds (II) (step 3). The compound (V) is obtained from the compound (IV) (step 4), then the compound (VIa) is obtained from the compound (V) (step 5). Further, the compound (VIb) is obtained from the compound (IVa) (step 6) and the compound (VII) is obtained from the compound (VI) (step 7). The desired compound (I) is obtained from the resultant compound (VII) (step 8).

Step 1:

The compound (IIa) having an $X^1$ in formula (II) of a halogen atom can be synthesized from the known starting material pyrrole-2-carboxylic acid or its derivatives (VIII) by the following steps:

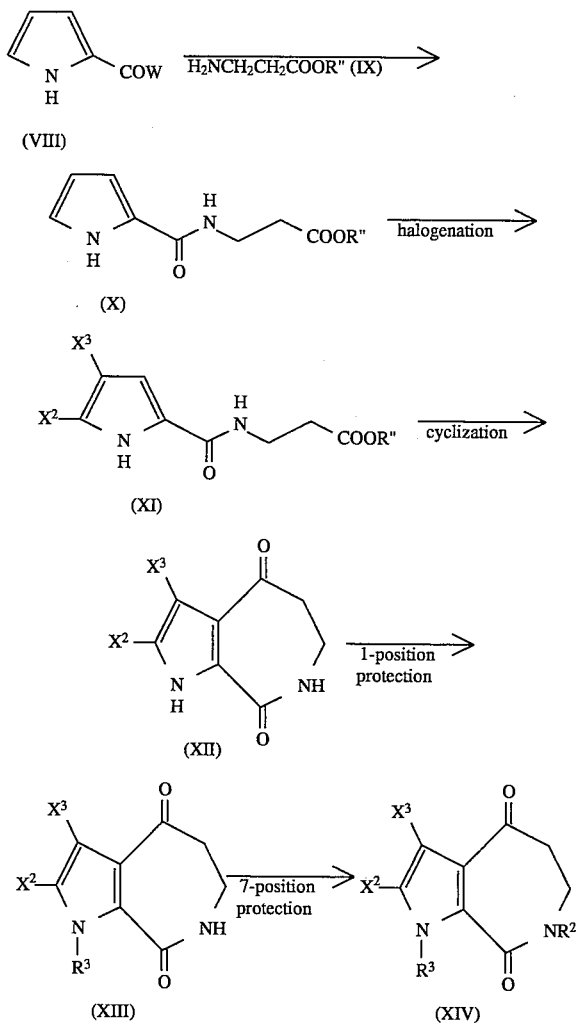

(wherein R" is a hydrogen atom or a protective group of a carboxyl group, $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsiloxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxy-methyl group, dimethyltexylsiloxymethyl group, or tert-butyldiphenylsiloxmethyl group, either one of $X^2$ and $X^3$ is a halogen atom and the other is a hydrogen atom, and W is a hydroxyl group or group which can be easily replaced by an amino group.)

In the above reaction, it is possible to produce the compound of the formula (X) by reacting the pyrrole-2-carboxylic acid having the formula (VIII) or its derivatives with the β-amino acid having the formula (IX) or its derivatives or their organic or inorganic salts.

The groups which can be easily replaced by an amino group for the group W of the compound (VIII) include a halogen atom, carboxylic acid residue, etc. Further, at the group R" of the compound (IX), as the protective group of the carboxyl group, a lower alkyl group preferably having 1 to 6 carbon atoms, particularly preferably 1 to 4 carbon atoms, such as a methyl group, ethyl group, propyl group, isopropyl group, n-butyl group, isobutyl group, or t-butyl group; aralkyl group of 7 to 20 carbon atoms such as a benzyl group or 9-anthrylmethyl group, and also the generally used protective groups described in "Protective Groups in Organic Synthesis" (T. W. Greene; John Wiley & Sons), etc. may be used.

Further, for the synthesis of the compound (X), the various methods described in the "Compendium for Organic Synthesis" (Wiley-Interscience; A Division of John Wiley & Sons) can be used. One example thereof is a method for treating pyrrole-2-carboxylic acid (W=OH in compound (VIII)) in the presence of an organic or inorganic base, and if necessary, by diethyl phosphate cyanide (DEPC), diphenyl phosphate azide (DPPA), dicyclohexylcarbodiimide (DCC), 1-ethyl-3-(3-dimethylaminopropyl)carbodiimide hydrochloride, 2-iodo-1-methylpyridinium iodide, etc. a method for converting 2-pyrrolecarboxylic acid by an ordinary method to an acid halide, a symmetric acid anhydride, a mixed acid anhydride, a p-nitrophenyl ester, or other active ester, followed by causing a reaction, etc. may be used.

Next, the resultant compound (X) is converted to (XI) by a halogenation reaction. This halogenation reaction may be performed by treating the compound (X) in an inert solvent such as methylene chloride, 1,2-dichloroethane, chloroform, acetonitrile, tetrahydrofuran, dioxane, ethylene glycol dimethyl ether, or dimethylformamide at a temperature of −50° to 100° C., preferably −10° to 60° C. with 0.3 to 1.2 equivalents of a halogenation agent such as N-chlorosuccinimide, trichloroisocyanuric acid, tert-butyl hypochlorite, iodine trichloride, N-bromosuccinimide, bromine, dioxane-bromine complex, 2,4,6,6-tetrabromo-2,5-cyclohexadiene, N-iodosuccinimide, iodine, iodine/potassium iodide, iodine/periodic acid, iodine-morpholine complex, iodine monochloride, or iodine monochloride/zinc chloride for 1 to 12 hours.

The resultant compound (XI) is treated, if necessary, by the action of an acid or base or by a suitable means such as catalytic reduction to remove the protective groups, then is subjected to a cyclization reaction. The cyclization reaction is performed by treating the compound (XI) with an organic acid such as methanesulfonic acid or an inorganic acid such as sulfuric acid or polyphosphoric acid or by a mixture thereof with phosphorus pentaoxide at room temperature to 170° C., preferably 80° to 130° C. In this case, if necessary, a solvent which is not interfering with the reaction may be added.

The resultant compound (XII) may be converted into the compound (XIII) by treatment in an inert solvent such as dimethylformamide, dimethylsulfoxide, tetrahydrofuran, ethylene glycol dimethyl ether, dioxane, benzene, toluene, or xylene in the presence of a base such as sodium hydroxide, potassium hydroxide, or potassium tert-butoxide at a temperature of −50° to 100° C., preferably −20° to 60° C., with 0.8 to 1.5 equivalents, with respect to compound (XII), of trimethylsilylethoxymethyl chloride, benzyloxymethyl chloride, p-methoxybenzyloxymethyl chloride (Kozikowski, A. et al: Tetrahedron Lett,. 28, 5125 (1987)), tert-butyldimethylsiloxymethyl chloride, dimethyltexylsiloxymethyl chloride, or tert-butyldiphenylsiloxymethyl chloride (Benneche, T. et al; Acta Chem. Scan., 43, 706 (1989)) for 1 to 12 hours.

The resultant compound (XIII) may be converted into the compound (XIV) by treatment in an inert solvent such as dimethylformamide, dimethylsulfoxide, tetrahydrofuran, ethylene glycol dimethyl ether, dioxane, benzene, toluene, or xylene at a temperature of −50° to 100° C., preferably −20° to 60° C., in the presence of a base such as sodium hydroxide, potassium hydroxide, or potassium tert-butoxide, with 0.8 to 1.5 equivalents of trimethylsilylethoxymethyl chloride, benzyloxymethyl chloride, p-methoxybenzyloxymethyl chloride, chloromethylmethyl ether, 2-methoxyethoxymethyl chloride, tert-butoxymethyl chloride, p-anisyloxymethyl chloride, guaiacolmethyl chloride, tert-butyldimethylsiloxymethyl chloride, dimethyltexylsiloxymethyl chloride, or tert-butyldiphenylsiloxymethyl chloride ("Protective Groups in Organic Synthesis" (T. W. Greene; John Wiley & Sons) for 1 to 12 hours.

The resultant compound (XIV) is separated and purified by a purification method generally used, for example, column chromatography, to obtain the compound having the formula (IIa):

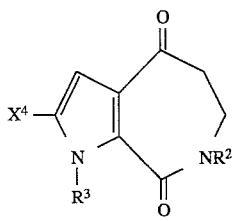

(IIa)

(wherein $R^2$ and $R^1$ are as defined above and $X^4$ is a halogen atom.)

Note that by separating from the mixture (XIII) the compound having an $X^2$ of a halogen atom and an $X^3$ of a hydrogen atom and using it for the next process, it is also possible to obtain the compound of the formula (IIa).

Further, when obtaining a compound (XIV) where the substituents $R^2$ and $R^3$ are identical, it is possible to protect the 1-position and the 7-position by a single process by the method similar to the process for producing the compound (XIII) from the compound (XII).

The compounds obtained by these reactions may be used as they are for the next processes, but if necessary, they may also be used after purification by a purification method generally used, for example, recrystallization or column chromatography.

Step 2:

It is possible to synthesize the compound (IIb) having an $X^1$ in the formula (II) of a hydrogen atom from the known starting material aldisin (XV):

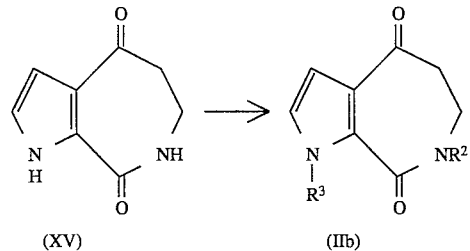

(wherein $R^2$ and $R^3$ are as defined above.)

The starting aldisin (XV) is a known compound described in Prager, R. et al: Aust. J. Chem., 43, p. 355 to 365 (1990). It may be prepared in the same way as the method for obtaining the compound (XIV) from the compound (XII) of the step 1.

The resultant compound (IIb) may be used as is for the next step, but if necessary, it may also be used after purification by a purification method generally used, for example, recrystallization or column chromatography.

Step 3:

It is possible to obtain the compound having the formula (IV) by causing a dialkyl phosphonoacetic acid ester (III) to react with the compound of the formula (II) obtained in the Step 1 or 2:

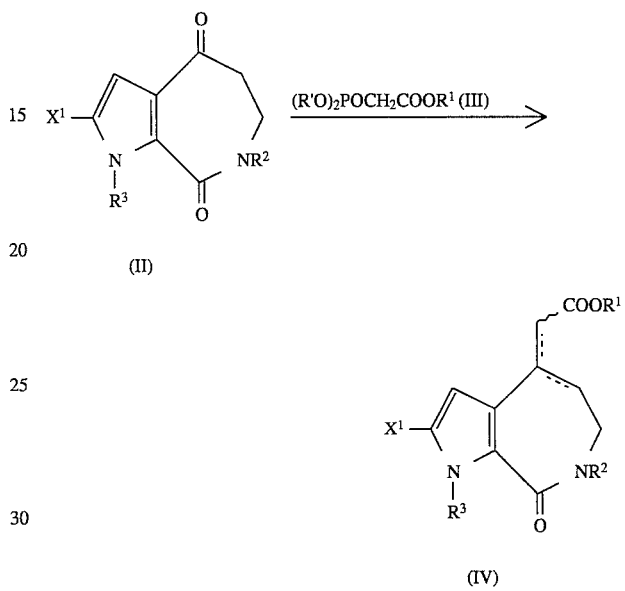

(wherein $R^1$, R2, $R^3$, and $X^1$ are as defined above, R' is a substitutable alkyl group of 1 to 4 carbon atoms, and the dotted line indicates a single bond existing at one or the other position.)

This step may be performed by causing a reaction in an inert solvent such as tetrahydrofuran, dioxane, ethylene glycol dimethyl ether, benzene, toluene, xylene, or dimethylformamide in the presence of a base such as sodium hydroxide, potassium hydroxide, sodium methoxide, sodium ethylate, or potassium tert-butoxide at a temperature of 0° to 120° C., preferably room temperature to 70° C., with 1 to 10 equivalents, with respect to compound (II), of trimethyl phosphonoacetate, methyldiethyl phosphonoacetate, ethyldimethyl phosphonoacetate, methyldiisopropyl phosphonoacetate, ethyldiethyl phosphonoacetate, isopropyldiethyl phosphonoacetate, tert-butyldiethyl phosphonoacetate, methyl bis(2,2,2-trifluoroethyl) phosphonoacetate, and other dialkyl phosphonoacetic acid esters for 3 to 36 hours.

The compound (IV) obtained by the above method can be used as it is as a material for producing the compound (V), but when necessary it is possible to separate the compound (IVa) used in the step 6 by column chromatography for example, purify it, and then use that.

Step 4:

It is possible to obtain the compound of the formula (V) by oxidizing the compound of the formula (IV) obtained in the step 3:

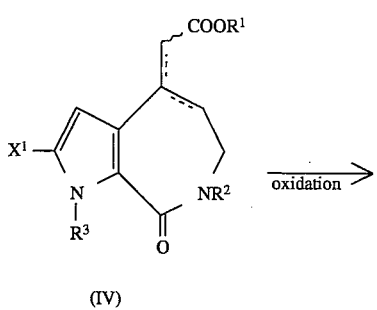

(IV)

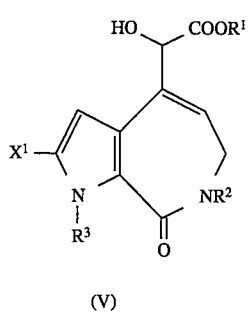

(V)

(wherein $R^1$, $R^2$, $R^3$, and $X^1$ are as defined above and the dotted lines show a single bond present at either one of the positions.)

This step may be performed by causing a reaction in an inert solvent such as tetrahydrofuran, diethyl ether, diethylene glycol dimethyl ether, or toluene in the presence of a strong base such as potassium bis(trimethylsilyl)amide, sodium bis(trimethylsilyl) amide, lithium bis(trimethylsilyl)amide, or lithium diisopropylamide, at a temperature of $-100°$ to $20°$ C., preferably $-78°$ to $0°$ C., with 1 to 1.5 equivalents, with respect to compound (IV), of an oxidizing agent such as 2-benzenesulfonyl-3-phenyloxaziridine (Davis, F. et al: J. Org. Chem., 53, 2087 (1988)), oxodiperoxymolybdenum (pyridine)(hexamethylphosphoric triamide) complex (Vedejs, E. et al: J. Org. Chem., 43, 188 (1978)), or molecular oxygen (Wasserman, H. et al: Tetrahedoron Lett., 1731 (1975)) for 1 to 12 hours.

The compound (V) obtained by the above method may be used as it is as the material for producing the compound (VIa), but if necessary, it may also be used after purification by a purification method generally used, for example, column chromatography.

Step 5:

It is possible to obtain the compound having the formula (VIa) by sulfonylizing the hydroxyl group of the compound (V) obtained in the step 4:

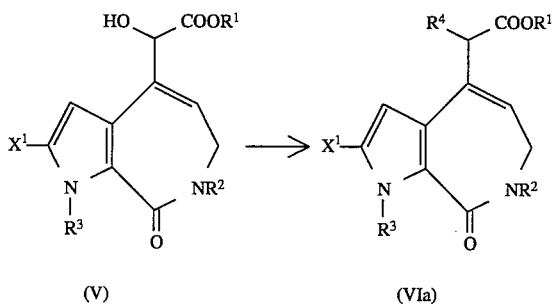

(V)  (VIa)

(wherein $R^1$, $R^2$, $R^3$, and $X^1$ are as defined above, $R^4$ is an alkylsulfonyloxy group or arylsulfonyloxy group, preferably the alkyl group includes an alkyl group having 1 to 4 carbon atoms or a halogen substituted methyl group, preferably, as the halogen, a fluorine atom or chlorine atom, preferably the aryl group includes a phenyl group p-tolyl group, 4-methoxyphenyl group, 4-chlorophenyl group, or nitrophenyl group.)

This step may be performed by causing a reaction in an inert solvent such as methylene chloride, 1,2-dichloroethane, chloroform, carbon tetrachloride, acetonitrile, diethyl ether, tetrahydrofuran, dioxane, benzene, toluene, xylene, or ethyl acetate in the presence of a base such as triethylamine, diisopropylethylamine, pyridine, sodium carbonate, sodium hydrogen carbonate, potassium carbonate or potassium hydrogencarbonate at a temperature of $-20°$ to $100°$ C., preferably $-10°$ to $60°$ C., with 1 to 10 equivalents, with respect to compound (V), of a sulfonylating agent such as methanesulfonyl chloride, methanesulfonic anhydride, ethanesulfonyl chloride, 1-propanesulfonyl chloride, 1-butanesulfonyl chloride, trifluoromethanesulfonyl chloride, trifluoromethanesulfonic anhydride, trichloromethanesulfonyl chloride, α-toluenesulfonyl chloride, benzenesulfonyl chloride, p-toluenesulfonyl chloride, p-toluenesulfonic anhydride, 4-methoxybenzenesulfonyl chloride, 4-chlorobenzenesulfonyl chloride, 2-nitrobenzenesulfonyl chloride, 3-nitrobenzenesulfonyl chloride, or 4-nitrobenzenesulfonyl chloride for 30 minutes to 12 hours.

The compound (VIa) obtained by the above method may be used as it is, as the material for producing the compound (VII), but if necessary, it may also be used after purification by a purification method generally used, for example, column chromatography.

Step 6:

It is possible to obtain the compound having the formula (VIb) where in the formula (VI) the $R^6$ is a halogen atom by halogenating the compound having the formula (IVa) obtained by separation of the compound (IV) obtained in the step 3:

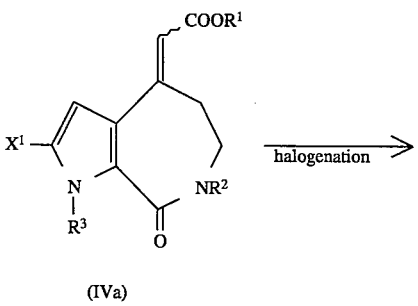

(IVa)

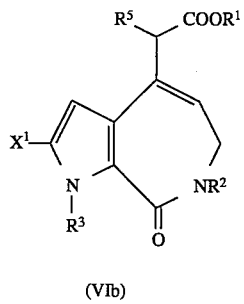

(VIb)

(wherein $R^1$, $R^2$, $R^3$, and $X^1$ are as defined above and $R^5$ is a halogen atom.)

This step may be performed by treating the compound (IVa) in an inert solvent such as methylene chloride, 1,2-dichloroethane, chloroform, acetonitrile, tetrahydrofuran, dioxane, ethylene glycol dimethyl ether, or dimethylformamide at $-50°$ to $120°$ C., preferably $-20°$ to $80°$ C., with 0.3 to 1.2 equivalents of a halogenating agent such as N-chlorosuccinimide, trichloroisocyanuric acid, tert-butyl hypochlorite, iodine trichloride, N-bromosuccinimide, bromine, dioxane-bromine complex, 2,4,6,6-tetrabromo-2,5-cyclohexadiene, N-iodosuccinimide, iodine, iodine/potassium iodide, iodine/periodic acid, iodine-morpholine complex, iodine monochloride, or iodine monochloride/zinc chloride for 1 to 12 hours.

The compound (VIb) obtained by the above method may be used as it is, as the material for producing the compound (VII), but if necessary, it may also be used after purification by a purification method generally used, for example, column chromatography.

Step 7:

It is possible to obtain the compound having the formula (VII) by reacting the compound having the formula (VI) obtained in the step 5 or 6 with guanidine:

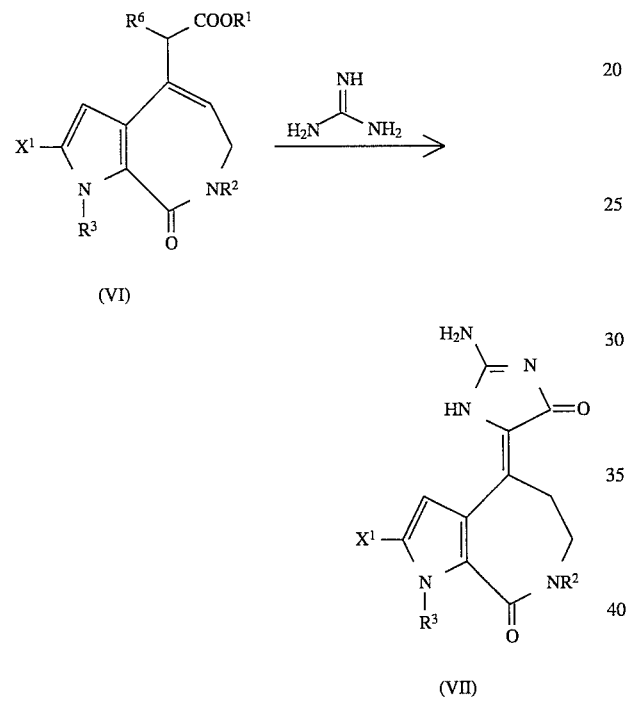

(wherein $R^1$, $R^2$, $R^3$, and $X^1$ are as defined above, and $R^6$ is an alkylsulfonyloxy group, arylsulfonyloxy group, or halogen atom.)

This step may be performed by causing a reaction with the compound (VI) in an inert solvent such as benzene, toluene, xylene, tetrahydrofuran, dioxane, ethylene glycol methyl ether, dimethylformamide, or dimethylsulfoxide at a temperature of 0° to 200° C., preferably room temperature to 120° C., with 1 to 10 equivalents of guanidine for 2 to 24 hours.

The compound (VII) obtained by the above method may be used as it is, as the material for producing the compound (I), but if necessary it may also be used after purification by a purification method generally used, for example, recrystallization or column chromatography.

Regarding the configuration of double bond portion of the 4-position of the compound (VII), the Z-configuration was confirmed, for example, from the fact that the signal of the 5-position methylene proton in proton NMR shifts to the low magnetic field side due to anisotropic effect of the spatially close carbonyl group. Further, this result can be confirmed from the conversion of the compound (VII) to the compound (I).

Step 8:

It is possible to obtain the compound having the formula (I) by removing the protection of the compound having the formula (VII) obtained in the step 7:

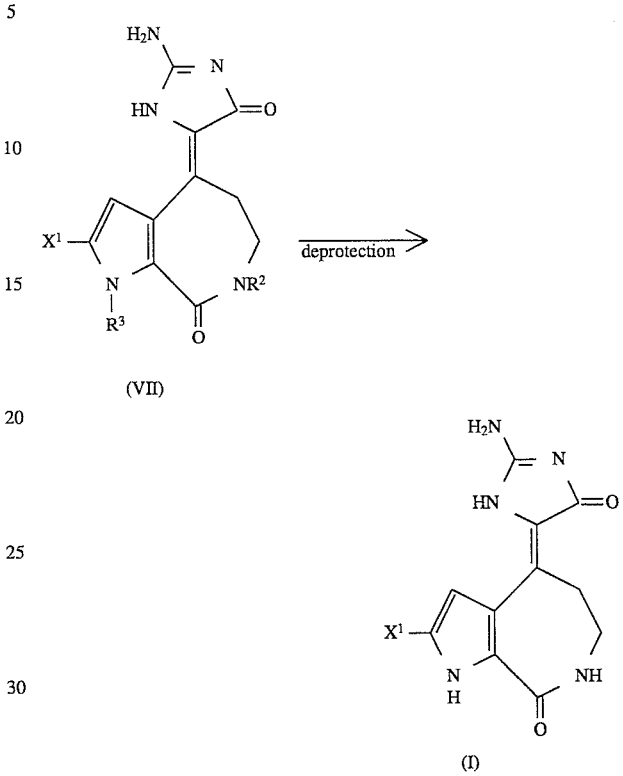

(wherein $R^2$, $R^3$, and $X^1$ are as defined above.)

This step may be performed by causing a reaction at a temperature of −50° to 150° C., preferably −20° to 120° C., of the compound (VII) with 1 to 10 equivalents of tetrabutylammonium fluoride/tetrahydrofuran, 1 to 10 equivalents of tetrabutylammonium fluoride/ethylenediamine, 1 to 10 equivalents of methanol/hydrochloric acid, 1 to 10 equivalents of ethanol/hydrochloric acid, etc. or by treatment with 1 to 10 equivalents of boron trifluoride ether complex, 1 to 10 equivalents of trifluoroacetic acid, catalytic reduction (Pd-C, hydrogen, 1 atm), etc., then treatment with 5 to 20 equivalents of benzyltrimethylammonium hydroxide, 5 to 20 equivalents of triethylamine, etc., or oxidation by 1 to 10 equivalents of 2,3-dichloro-5,6-dicyano-1,4-benzoquinone (DDQ).

Further, this step may be performed by general deprotection methods such as a method of using an acid catalyst, the catalytic reduction method, and oxidation, for example, the various methods as described in "Protective Groups in Organic Synthesis" (T. W. Greene; John Wiley & Sons), etc.

The compound (I) obtained by the above method may be purified by a purification method generally used, for example, recrystallization or column chromatography.

Note that the compound (I) may be obtained as a pharmaceutically acceptable salt according to an ordinary method, for example, an acid addition salt of the compound having the formula (I) may be produced by reacting the same by an ordinary method with an inorganic acid such as hydrochloric acid, nitric acid, sulfuric acid, hydrobromic acid, or phosphoric acid or an organic acid such as maleic acid, fumaric acid, tartaric acid, citric acid, lactic acid, oxalic acid, acetic acid, benzoic acid, methanesulfonic acid, p-toluenesulfonic acid, adipic acid, palmitic acid, and tannic acid.

EXAMPLES

The present invention will now be further illustrated by, but is by no means limited to, the following Reference Examples and Examples.

Reference Example 1

Synthesis of methyl 3-(pyrrol-2-ylcarbonylamino)propionate (1)

i) A 0.2 ml amount of dimethylformamide and 19.6 ml of thionyl chloride were dropwise added under room temperature to a 100 ml toluene suspension of 20 g of pyrrole-2-carboxylic acid. The mixture was stirred at 60° C. for 2 hours, then the solvent was distilled off under reduced pressure and the residue was dried under reduced pressure to obtain crude crystals of pyrrole-2-carbonyl chloride.

ii) A 76.6 ml amount of trimethylamine was gradually dropwise added under ice cooling to a 100 ml methylene chloride suspension of 30.7 g of β-alaninemethylester hydrochloride. The mixture was stirred at room temperature for 1 hour. Then, a 200 ml methylene chloride solution of pyrrole-2-carbonyl chloride obtained in the above process i) was gradually dropwise added under ice cooling. The mixture was stirred at room temperature for 3 hours. A 200 ml amount of water was added to the reaction solution, the mixture was stirred, then the methylene chloride layer was removed and washed by 200 ml of 5% hydrochloric acid, then 250 ml of a saturated aqueous solution of sodium hydrogen carbonate. The organic layer was dried, filtered, and then concentrated under reduced pressure to obtain crude crystals which were then recrystallized from methylene chloride/methanol to obtain 22 g of the above-referenced compound (1) (yield 62%).

Reference Example 2

Synthesis of methyl 3-(2-bromopyrrol-5-ylcarbonylamino)propionate and methyl 3-(3-bromopyrrol-5-ylcarbonylamino)propionate (2)

A 907 mg amount of N-bromosuccinimide was added under ice cooling to an 18 ml tetrahydrofuran solution of 1 g of the compound (1) synthesized in Reference Example 1. The mixture was stirred under ice cooling for 2 hours, then under room temperature for a further 2 hours. The solvent was distilled off under reduced pressure, then the residue was purified by silica gel column chromatography (hexane: ethyl acetate=3:1) to obtain 0.975 g of a mixture of the above-referenced compounds (2) (yield 70%).

Reference Example 3

Synthesis of 3-(2-bromopyrrol-5-ylcarbonylamino)propionic acid and 3-(3-bromopyrrol-5ylcarbonylamino)propionic acid (3)

A 25 ml amount of a 10% aqueous solution of potassium hydroxide was dropwise added under ice cooling to a 20 ml dioxane solution of 1.6 g of the mixture of the compounds (2) synthesized in Reference Example 2. The mixture was stirred at room temperature for 3 hours, then the reaction solution was adjusted by concentrated hydrochloric acid to a pH of 3 under ice cooling and extraction was performed by ethyl acetate. The extract was dried, filtered, then concentrated under reduced pressure to obtain crude crystals which were then recrystallized from isopropyl ether to obtain 1.3 g of a mixture of the above-referenced compounds (3) (yield 86%).

Reference Example 4

Synthesis of 2-bromo- 6,7-dihydropyrrolo[2,3-c] azepin-4,8(1H,5H)dione and 3-bromo-6,7-dihydro-pyrrol[2,3-c]azepin-4,8(1H,5H)dione (4)

A 0.1 g amount of phosphorus pentaoxide was added to 15 g of polyphosphoric acid, then was stirred at 120° C. for 1 hour. The temperature was lowered once to 100° C., then 3 g of the mixture of the compounds (3) synthesized in Reference Example 3 was added. The mixture was stirred at 100° C. for 1 hour, then the reaction mixture was cooled to room temperature. Ice was added to the reaction mixture under ice cooling, then a 10% aqueous solution of sodium hydroxide was used to adjust the pH to 5. Extraction was performed by ethyl acetate, then the extract was dried, filtered, and concentrated under reduced pressure to obtain 1.9 g of the mixture of the above-referenced compounds (4) (yield 68%).

Reference Example 5

Synthesis of 2-bromo-1-trimethylsilylethoxymethyl-6,7-dihydropyrrolo[2,3-c]azepin-4,8(1H, 5H)dione (5) and 3-bromo-1-trimethylsilylethoxymethyl-6,7-dihydropyrrol[2,3-c]azepin-4,8(1H, 5H)-dione (6)

A 5 g amount of the mixture of the compounds (4) synthesized in Reference Example 4 was gradually added under ice cooling to a 100 ml dimethylformamide suspension of 0.87 g of sodium hydride (60% oil). The mixture was stirred at room temperature for 1 hour. A 3.7 ml amount of trimethylsilylethoxymethyl chloride was dropwise added under ice cooling, the mixture was stirred at room temperature for 2 hours, then a saturated aqueous solution of ammonium chloride was added and extraction was performed by ethyl acetate. The extract was washed with saturated saline, dried, filtered, and concentrated under reduced pressure to obtain a mixture of the above-referenced compounds which were then separated and purified by silica gel column chromatography (hexane:ethyl acetate=4:1 to 2:1) to obtain 2.7 g of the above-referenced compound (5) (yield 35%) and 1.8 g of the above-referenced compound (6) (yield 23%). Further, the crude crystals of the above-referenced compounds (5) and (6) were recrystallized from hexane/ether to obtain 2.2 g of purified crystals of (5) and 1.4 g of purified crystals of (6), respectively.

Reference Example 6

Synthesis of 2-bromo-1,7-di(trimethylsilylethoxymethy)-6,7-dihydropyrrolo[2,3-c]azepin-4,8(1H, 5H)dione (7)

A 5 ml dimethylformamide solution of 740 mg of the compound (5) synthesized in Reference Example 5 was dropwise added under ice cooling to a 10 ml dimethylformamide suspension of 87.3 mg of sodium hydride (60% oil). The mixture was stirred at room temperature for 1 hour. A 0.39 ml amount of trimethylsilylethoxymethyl chloride was dropwise added under ice cooling, the mixture was stirred at room temperature for 2 hours, then a saturated aqueous solution of ammonium chloride was added and extraction was performed by ethyl acetate. The extract was washed with saturated saline, dried, filtered, and concentrated under reduced pressure to obtain a residue which was purified by silica gel column chromatography (hexane:ether=2:1) to obtain 450 mg of the above-referenced compound (7) (yield 45%).

Reference Example 7

Synthesis of 1,7-di(trimethylsilylethoxymethyl)-6,7-dihydropyrrolo[2,3-c]azepin-4,8(1H, 5H)dione (8)

A 500 mg amount of the 6,7-dihydropyrrolo[2,3-c]azepin-4,8(1H, 5H)dione (aldisin) described in the reference (Prager, R. et al: Aust. J. Chem., 43, p. 355–365 (1990)) was added to a 20 ml dimethylformamide suspension of 252 mg of sodium hydride (60% oil). The mixture was stirred at room temperature for 1 hour. A 1.12 ml amount of trimethylsilylethoxymethyl chloride was added under ice cooling, the mixture was stirred at room temperature for 3 hours, then a saturated aqueous solution of ammonium chloride was added and extraction was performed by ethyl acetate. The extract was washed with saturated saline, dried, filtered, and concentrated under reduced pressure to obtain a residue which was purified by silica gel column chromatography (hexane:ether acetate=6:1) to obtain 623 mg of the above-referenced compound (8) (yield 48%).

Example 1

Synthesis of 2-bromo-4-ethoxycarbonylylidene-1,7-di(triethylsilylethoxymethyl)-4,5,6,7-tetrahydropyrrolo[2,3-c]azepin-8-one (9) and 2-bromo-4-ethoxy-carbonylmethyl-1,7-di(trimethylsilyl-ethoxymethyl)-6,7-dihydropyrrolo[2,3-c]azepin-8-one (10)

A 0.86 ml amount of ethyl diethyl phosphonoacetate was dropwise added under ice cooling to a 4 ml ethylene glycol dimethyl ether suspension of 173 mg of sodium hydride (60% oil). The mixture was stirred at room temperature for 1 hour, then a 3 ml ethylene glycol dimethyl ether solution of 435 mg of the compound (7) synthesized in Reference Example 6 was dropwise added and the mixture was stirred at 50° C. for 24 hours. A saturated aqueous solution of ammonium chloride was added and extraction was performed with ether. The extract was washed with saturated saline, dried, filtered, and concentrated under reduced pressure to obtain the above-referenced compound which was then separated and purified by silica gel column chromatography (hexane:ether=2:1) to obtain 107 mg of the above-referenced compound (9) (yield 22%) and 304 mg of the above-referenced compound (10) (yield 61%).

Example 2

Synthesis of 4-ethoxycarbonylylidene-1,7-di(trimethylsilylethoxymethyl)-4,5,6,7-tetrahydro-pyrrol[2,3-c]azepin-8-one (11) and 4-ethoxycarbonyl-methyl-1,7-di(trimethylsilylethoxymethyl)-6,7-dihydropyrrolo[2,3-c]azepin-8-one (12)

The same procedure was followed as in Example 1 to obtain 205 mg of the above-referenced compound (11) (yield 25%) and 470 mg of the above-referenced compound (12) (yield 58%) from 700 mg of the compound (8) synthesized in Reference Example 7, 329 mg of sodium hydride (60% oil), and 1.63 ml of ethyl diethyl phosphonoacetate.

Example 3

Synthesis of 2-bromo-4-ethoxy-carbonylhydroxymethyl-1,7-di(trimethylsilylethoxymethyl)-6,7-dihydropyrrolo[2,3-c]azepin-8-one (13)

A 394 mg amount of a mixture of the compounds (9) and (10) synthesized in Example 1 was dissolved in 8 ml of tetrahydrofuran, then 1.51 ml of potassium bis(trimethylsilyl)amide (0.5 mole/toluene solution) was gradually dropwise added at −78° C. The mixture was stirred at the same temperature for 20 minutes, then 198 mg of 2-benzenesulfonyl-3-phenyloxaziridine (Davis, F. et al: J. Org. Chem., 53, 2087 (1988)) was added and the resultant mixture was stirred for a further 3 hours. A saturated aqueous solution of ammonium chloride was added and extraction was performed with ether. The extract was washed with saturated saline, dried, filtered, and concentrated under reduced pressure to obtain a residue which was then purified by silica gel column chromatography (hexane:ether=3:2) to obtain 315 mg of the above-referenced compound (13) (yield 78%).

Example 4

Synthesis of 4-ethoxycarbonylhydroxy-methyl-1,7-di(trimethylsilylethoxymethyl)-6,7-dihydropyrrolo[2,-c]azepin-8-one (14)

A 135 mg amount of the above-referenced compound (14) (yield 72%) was obtained from 182 mg of a mixture of the compound (11) and (12) synthesized in Example 2, 0.88 ml of potassium bis(trimethylsilyl)amide (0.5 mol/toluene solution), and 106 mg of 2-benzenesulfonyl-3-phenoyloxaziridine, in the same manner as in Example 3.

Example 5

Synthesis of 2-bromo-4-ethoxycarbonyl(methanesulfonyloxy) methyl-1,7-di(trimethylsilylethoxymethyl)-6,7-dihydropyrrolo [2,3-c]azepin-8-one (15)

A 0.046 ml amount of methanesulfonyl chloride was dropwise added under ice cooling to a 5 ml methylene chloride solution of 295 mg of the compound (13) synthesized in Example 3 and 0.21 ml of triethylamine. The mixture was stirred at room temperature for 1 hour. A saturated aqueous solution of sodium hydrogen carbonate was added thereto and extraction was performed with methylene chloride. The extract was washed with saturated saline, dried, filtered, and concentrated under reduced pressure to obtain a residue which was then purified by silica gel column chromatography (hexane:ether=2:3) to obtain 331 mg of the above-referenced compound (15) (yield 99%).

Example 6

Synthesis of 4-ethoxycarbonyl(methanesulfonyloxy)methyl-1,7-di(trimethylsilyl-ethoxymethyl)-6,7-dihydropyrrolo[2,3-c]azepin-8-one (16)

A 940 mg amount of the above-referenced compound (16) (yield 97%) was obtained from 840 mg of the compound (14) synthesized in Example 4, 0.69 mgl of triethylamine, and 0.15 ml of methanesulfonyl chloride, in the same manner as in Example 5.

Example 7

Synthesis of 4-ethoxycarbonylbromomethyl-1,7-di(trimethylsilylethoxymethyl)-6,7-dihydropyrrolo[2,3-c]azepin-8-one (17)

A 39 mg amount of N-bromosuccinimide was added under ice cooling to a 2 ml tetrahydrofuran solution of 99 mg of the compound (11) synthesized in Example 2. The mixture was stirred at room temperature for 5 hours. The solvent was distilled off under reduced pressure to obtain a residue which was then purified by silica gel column chromatography (hexane:ether=2:1) to obtain 69 mg of the above-referenced compound (17) (yield 60%).

Example 8

Synthesis of 4-(2-amino-4-oxo-2-imidazolin-5-ylidene)-2-bromo-1,7-di(trimethyl-silylethoxymethyl)-4,5,6,7-tetrahydropyrrolo[2,3-c]azepin-8-one (18)

A 5 ml dimethylformamide solution of 325 mg of the compound (15) synthesized in Example 5 and 143 ml of guanidine was stirred at 50° C. for 6 hours. The solvent was distilled off under reduced pressure to obtain a residue which was then purified by silica gel column chromatography (methylene chloride:methanol=15:1). The solvent was distilled off under reduced pressure, then the crude crystals were recrystallized from hexane/ether to obtain 120 mg of the above-referenced compound (18) (yield 42%).

Example 9

Synthesis of 4-(2-amino-4-oxy-2-imidazolin-5-ylidene)-1,7-di(trimethylsilyl-ethoxymethyl)-4,5,6,7-tetrahyropyrrolo[2,3-c]azepin-8one (19)

A 420 mg amount of the above-referenced compound (19) was obtained from 935 mg of the compound (16) synthesized in Example 6 and 281 mg of guanidine to obtain the crude crystals in the same manner as in Example 8 followed by, recrystallizing from ether/methanol (yield 50%).

Example 10

Synthesis of 4-(2-amino-4-oxy-2-imidazolin-5-ylidene)-2-bromo-4,5,6,7-tetrahydropyrrolo[2,3-c]azepin-8-one (hymenialdisine) hydrochloride (20)

A 3 ml amount of 10% hydrochloric acid was added to a 3 ml methanol solution of 300 mg of the compound (18) synthesized in Example 8. The mixture was stirred at 90° C. for 1 hour. The solvent was distilled off under reduced pressure to obtain a residue which was then purified by silica gel column chromatography (chloroform:methanol: 2% acetic acid=65:35:10). The solvent was distilled off under reduced pressure, then the residue was treated by 1 ml of isopropyl alcohol saturated with hydrochloric acid to give the crude crystals which were recrystallized by methanol/ether to obtain 150 mg of the above-referenced compound (20) (yield 81%).

Example 11

Synthesis of 4-(2-amino-4-oxy-2-imidazolin-5-ylidene)-4,5,6,7-tetrahydropyrrolo[2,3-c]azepin-8-one (debromohymenialdisine) hydrochloride (21)

A 0.5 ml amount of trifluoroacetic acid was dropwise added under ice cooling to a 3.5 ml methylene chloride solution of 105 mg of the compound (19) synthesized in Example 9. The mixture was stirred at room temperature for 20 minutes. The solvent was distilled off under reduced pressure, then the residue was dissolved in 5 ml of 50% acetic acid/0.05 ml of concentrated hydrochloric acid and stirred at 90° C. for 1 hour. The solvent was again distilled off under reduced pressure, then the residue was dissolved in 5 ml of methanol/1 ml of triethyl amine and the resultant mixture was stirred at 100° C. for 3 hours. The solvent was distilled off under reduced pressure, then the residue was purified by the same procedure as in Example 10 to obtain 42 mg of the above-referenced compound (21) (yield 75%).

The physicochemical data of the compounds obtained in the above Reference Examples is shown in Table 1 and the physicochemical data of the compounds obtained in the Examples of the present invention is shown in Table 2.

TABLE 1

| Compound No. | Chemical structure | Properties m.p. | IR | NMR |
|---|---|---|---|---|
| 1 | (structure with pyrrole-N-H, CH=CH-C(=O)-NH-CH$_2$CH$_2$-COOMe) | Colorless crystals m.p. 129–130° C. | (CHCl$_3$) 3453, 1734, 1640, 1558, 1516, 1439, 1316 | $^1$H-NMR(CDCl$_3$) 2.63(2H, t), 3.68(2H, t), 3.71(3H, s), 6.23(1H, dd), 6.5(1H, brs), 6.56(1H, m), 6.92(1H, m), 9.4(1H, brs) |
| 2 | (structure with Br-pyrrole-N-H, CH=CH-C(=O)-NH-CH$_2$CH$_2$-COOMe) | Colorless crystals | (CHCl$_3$) 3444, 1726, 1648, 1558, 1516, 1439, 1045, 926 | $^1$H-NMR(CDCl$_3$) 2.62 and 2.64(total 2H, each t), 3.66(2H, t), 3.71 and 3.72(total 3H, each s), 6.16 and 6.54(total 1H, each d), 6.49 and 6.9(total 1H, d and dd), 6.48 and 6.55(total 1H, each brs), 9.38 and 10.35 (total 1H, each brs) |
| 3 | (structure with Br-pyrrole-N-H, CH=CH-C(=O)-NH-CH$_2$CH$_2$-COOH) | Colorless crystals | (KBr) 3454, 3164, 2957, 1712, 1612, 1570, 1516, 1434, 1406, 1324, 1220, 1045 | $^1$H-NMR(d$_6$-DMSO) 2.47(2H, t), 3.4(2H, t), 6.11 and 6.82(total 1H, each d), 6.72 and 6.97(total 1H, d and dd), 8.05 and 8.16(total 1H, each t) |

TABLE 1-continued

| Compound No. | Chemical structure | Properties m.p. | IR | NMR |
|---|---|---|---|---|
| 4 | (structure: bromo-pyrrole fused with azepinedione, NH, NH) | Colorless crystals | (KBr) 3460, 3347, 1667, 1645, 1546, 1460, 1365, 1258, 892 | $^1$H-NMR(d$_6$-DMSO) 2.7(2H, m), 3.35(2H, m), 6.55 and 7.18(total 1H, s and d), 8.37 and 8.44(total 1H, both m), 12.5 and 12.9 (total 1H, both brs) |
| 5 | (structure with Br, Me$_3$Si-CH$_2$CH$_2$-O-CH$_2$- on N, NH) | Colorless crystals m.p. 86–87° C. | (CHCl$_3$) 3418, 1658, 1526, 1464, 1251, 1086, 838 | $^1$H-NMR(CDCl$_3$) −0.038(9H, s), 0.89(2H, t), 2.84(2H, m), 3.5–3.6(4H, m), 5.9(2H, s), 6.79(1H, s), 6.86(1H, m) |
| 6 | (structure with Br, SEM on N, NH) | Colorless crystals m.p. 72–73° C. | (CHCl$_3$) 3416, 1660, 1478, 1483, 1251, 1096, 838 | $^1$H-NMR(CDCl$_3$) −0.01(9H, s), 0.93(2H, t), 2.86(2H, m), 3.49–3.61(4H, m), 5.69(2H, s), 6.6(1H, m), 7.15(1H, s) |
| 7 | (structure with Br, two SEM groups) | A colorless oil | (CHCl$_3$) 2955, 1644, 1525, 1450, 1251, 1077, 861, 838 | $^1$H-NMR(CDCl$_3$) −0.038(9H, s), 0.04(9H, s), 0.88(2H, t), 0.94(2H, t), 2.83(2H, m), 3.55(2H, t), 3.6(2H, t), 3.76(2H, m), 5.03(2H, s), 5.86(2H, s), 6.73(1H, s) |
| 8 | (structure with two SEM groups, no Br) | Colorless crystals | (CHCl$_3$) 3019, 2955, 1640, 1526, 1485, 1251, 1074 | $^1$H-NMR(CDCl$_3$) −0.01(9H, s), 0.03(9H, s), 0.92(2H, t), 0.95(2H, t), 2.87(2H, m), 3.57(2H, t), 3.63(2H, t), 3.8(2H, m), 5.05(2H, s), 5.74(2H, s), 6.73(1H, d), 7.07(1H, d) |

TABLE 2

| Compound No. | Chemical structure | Properties | IR | NMR | Mass |
|---|---|---|---|---|---|
| 9 | (structure with COOC$_2$H$_5$, Br, two SEM groups) | A colorless oil | (CHCl$_3$) 3018, 2955, 1700, 1636, 1612, 1475, 1435, 1224, 1208, 1077, 837 | $^1$H-NMR(CDCl$_3$) −0.04(9H, s), −0.016(9H, s), 0.82–0.98(4H, m), 1.29(3H, t), 3.37(2H, m), 3.47–3.64(6H, m), 4.16(2H, q), 4.95(2H, s), 5.76(2H, s), 6.01(1H, t), 6.38(1H, s) | FABMS C$_{24}$H$_{41}$N$_2$O$_5$$^{79}$Br(Si)$_2$+ (Li+H)+: 579.2 C$_{24}$H$_{41}$N$_2$O$_5$$^{81}$Br(Si)$_2$+ (Li+H)+: 581.2 |

TABLE 2-continued

| Compound No. | Chemical structure | Properties | IR | NMR | Mass |
|---|---|---|---|---|---|
| 10 | (structure with Br, Me$_3$Si-O-N-...-N-O-SiMe$_3$, COOC$_2$H$_5$) | A colorless oil | (CHCl$_3$) 3019, 1732, 1626, 1524, 1505, 1470, 1427, 1250, 1076, 837 | $^1$H-NMR(CDCl$_3$) −0.045(9H, s), −0.01(9H, s), 0.89(4H, m), 1.22(3H, t), 3.36(2H, m), 3.73(2H, d), 4.13(2H, q), 4.93(2H, s), 5.84(2H, s), 5.99(1H, t), 6.34(1H, s) | HRFABMS Calcd for C$_{24}$H$_{41}$N$_2$O$_6$$^{79}$Br(Si)$_2$+ (Li+H)$^+$: 579.1898; Found: 579.1913 Calcd for C$_{24}$H$_{41}$N$_2$O$_6$$^{81}$Br(Si)$_2$+ (Li+H)$^+$: 581.1877; Found: 581.1894 |
| 11 | (structure with COOC$_2$H$_5$, Me$_3$Si-O-N-...-N-O-SiMe$_3$) | A colorless oil | (CHCl$_3$) 2954, 1699, 1635, 1608, 1474, 1251, 1179, 1073, 861 | $^1$H-NMR(CDCl$_3$) −0.04(9H, s), −0.013(9H, s), 0.83−0.99(4H, m), 1.29(3H, t), 3.4(2H, m), 3.45−3.65(6H, m), 4.17(2H, q), 4.95(2H, s), 5.63(2H, s), 6.07(1H, t), 6.34(1H, d), 6.98(1H, d) | HRFABMS Calcd for C$_{24}$H$_{42}$N$_2$O$_5$(Si)$_2$+H$^+$: 495.2711; Found: 495.2717 |
| 12 | (structure with COOC$_2$H$_5$, Me$_3$Si-O-N-...-N-O-SiMe$_3$) | A colorless oil | (CHCl$_3$) 3007, 2954, 1730, 1624, 1466, 1251, 1072, 861 | $^1$H-NMR(CDCl$_3$) −0.04(9H, s), −0.008(9H, s), 0.9(4H, m), 1.21(3H, t), 3.4(2H, brs), 3.52(4H, m), 3.73(2H, d), 4.13(2H, q), 4.94(2H, s), 5.71(2H, s), 5.95(1H, t), 6.26(1H, d), 7.03(1H, d) | HRFABMS Calcd for C$_{24}$H$_{42}$N$_2$O$_5$(Si)$_2$+H$^+$: 495.2711; Found: 495.2734 |
| 13 | (structure with HO, COOC$_2$H$_5$, Br, Me$_3$Si-O-N-...-N-O-SiMe$_3$) | A colorless oil | (CHCl$_3$) 3526, 2954, 1731, 1628, 1469, 1445, 1250, 1079, 860 | $^1$H-NMR(CDCl$_3$) −0.05(9H, s), −0.001(9H, s), 0.83−0.95(4H, m), 1.13(3H, t), 3.29(1H, d), 3.52(4H, m), 3.72(1H, dd), 3.78(1H, dd), 4.17(2H, q), 4.89(1H, d), 4.9(1H, d), 4.96(1H, d) 5.83(2H, s), 6.17(1H, t), 6.47(1H, s) | HRFABMS Calcd for C$_{24}$H$_{41}$O$_6$N$_2$$^{79}$Br(Si)$_2$+ (Li+H)$^+$: 595.1846; Found: 595.1870 Calcd for C$_{24}$H$_{41}$O$_6$N$_2$$^{81}$Br(Si)$_2$+ (Li+H)$^+$: 597.1854 |

TABLE 2-continued

| Compound No. | Chemical structure | Properties | IR | NMR | Mass |
|---|---|---|---|---|---|
| 14 | (structure: pyrrole fused azepinone with HO-CH(COOC$_2$H$_5$)- substituent; N-SEM groups: Me$_3$Si-CH$_2$CH$_2$-O-CH$_2$-) | A colorless oil | (CHCl$_3$) 3502, 3014, 1728, 1625, 1467, 1251, 1074, 837 | $^1$H-NMR(CDCl$_3$) −0.05(9H, s), −0.01(9H, s), 0.88(2H, t), 0.92(2H, t), 1.1(3H, t), 3.28(1H, d), 3.5(2H, t), 3.53(2H, t), 3.72(1H, dd), 3.78(1H, dd), 4.62(2H, m), 4.89(1H, d), 4.94(1H, d), 4.97(1H, d), 5.7(2H, s), 6.14(1H, t), 6.39(1H, d), 7.02(1H, d) | HRFABMS Calcd for C$_{24}$H$_{42}$N$_2$O$_6$(Si)$_2$+H$^+$: 511.2660: Found: 511.2646 |
| 15 | (structure: 5-Br pyrrole fused azepinone with MeS(O)$_2$-O-CH(COOC$_2$H$_5$)- substituent; N-SEM groups) | A light yellow oil | (CHCl$_3$) 2955, 1755, 1632, 1470, 1446, 1368, 1250, 1176, 1081, 967 | $^1$H-NMR(CDCl$_3$) −0.04(9H, s), −0.006(9H, s), 0.83–0.9(4H, m), 1.15(3H, t), 3.15(3H, s), 3.47–3.59(4H, m), 3.77(2H, d), 4.18(2H, q), 4.87(1H, d), 4.99(1H, d), 5.72(1H, s), 5.76(1H, d), 5.95(1H, d), 6.3(1H, t), 6.49(1H, s) | — |
| 16 | (structure: pyrrole fused azepinone with MeS(O)$_2$-O-CH(COOC$_2$H$_5$)- substituent; N-SEM groups) | A light yellow oil | (CHCl$_3$) 3018, 2955, 1755, 1627, 1368, 1250, 1176, 1076, 860 | $^1$H-NMR(CDCl$_3$) −0.037(9H, s), −0.006(9H, s), 0.91(2H, t), 0.95(2H, t), 1.14(3H, t), 3.13(3H, s), 3.45–3.59(4H, m), 3.77(1H, d), 4.18(2H, m), 5.63(1H, d), 5.76(1H, d), 5.78(1H, s), 6.26(1H, t), 6.42(1H, d), 7.05(1H, d) | — |
| 17 | (structure: 5-Br pyrrole fused azepinone with Br-CH(COOC$_2$H$_5$)- substituent; N-SEM groups) | A colorless oil | — | $^1$H-NMR(CDCl$_3$) −0.035(9H, s), −0.006(9H, s), 0.82–0.9(4H, m), 1.22(3H, t), 3.45–3.6(4H, m), 3.62(2H, d), 4.18(2H, q), 4.85(1H, d), 4.96(1H, d), 5.25(1H, s), 5.7(1H, d), 5.73(1H, d), 6.4(1H, t), 6.48(1H, s) | — |

TABLE 2-continued

| Compound No. | Chemical structure | Properties | IR | NMR | Mass |
|---|---|---|---|---|---|
| 18 | 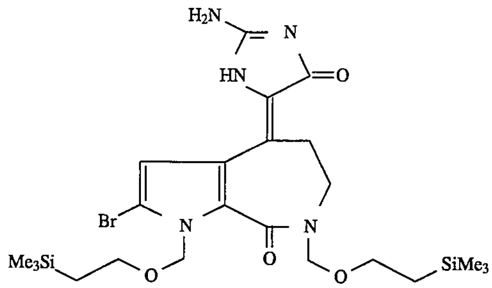 | Colorless crystals m.p. 115–117° C. | (CHCl₃) 3444, 3350, 2954, 1690, 1628, 1475, 1439, 1250, 1075, 837 | ¹H-NMR(CD₃OD) −0.06(9H, s), −0.03(9H, s), 0.86(2H, t), 0.9(2H, t), 3.37(2H, t), 3.5(2H, t), 3.54(2H, t), 3.66(2H, t), 4.95(2H, s), 5.72(2H, s), 6.57(1H, s) | HRFABMS Calcd for $C_{23}H_{38}N_5O_4{}^{79}Br(Si)_2{}^+$ (Li+H)⁺: 590.1806; Found: 590.1830 Calcd for $C_{23}H_{38}N_5O_4{}^{81}Br(Si)_2{}^+$ (Li+H)⁺: 592.1786; Found: 592.1826 |
| 19 | 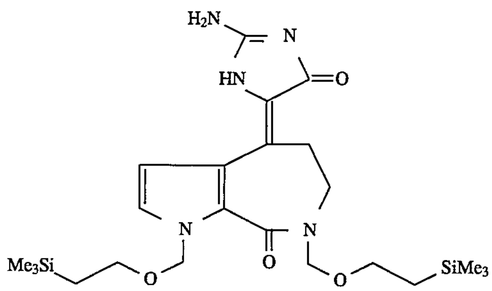 | Colorless crystals m.p. 125–127° C. | (CHCl₃) 3627, 3436, 3339, 3024, 2954, 1688, 1628, 1476, 1284, 1075, 837 | ¹H-NMR(CD₃OD) −0.06(9H, s), −0.03(9H, s), 0.86(2H, t), 0.91(2H, t), 3.39(2H, t), 3.49(2H, t), 3.51(2H, t), 3.61(2H, t), 4.98(2H, s), 5.62(2H, s), 6.43(1H, d), 7.25(1H, d) | HRFABMS Calcd for $C_{23}H_{38}N_5O_4(Si)_2{+}H^+$: 506.2619 Found: 506.2643 |
| 20 | 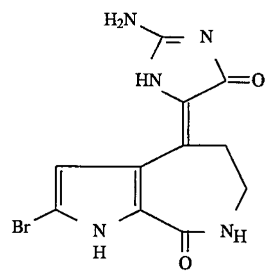 | Yellow crystals m.p. 240–242° C. (decomp.) | (KBr) 3400(br), 3255(br), 1747, 1708, 1628, 1542, 1483, 1366, 1275, 1175, 1122, 1054 | ¹H-NMR(CD₃OD) 3.5(4H, brs), 6.67(1H, s) ¹³C-NMR (CD₃OD) 32.6, 39.2, 105.7, 111, 120.9, 122.4, 127.6, 130, 154.6, 162.5, 163.7 | FABMS $C_{11}N_{10}N_6O_2{}^{78}Br+H^+$: 324 $C_{11}N_{10}N_6O_2{}^{81}Br+H^+$: 326 |
| 21 | 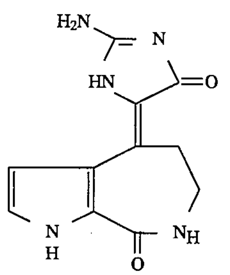 | Yellow crystals m.p. 235–238° C. (decomp.) | (KBr) 3420(br), 3248(br), 1748, 1712, 1640, 1538, 1476, 1429, 1359, 1264, 1117, 788 | ¹H-NMR(CD₃OD) 3.37–3.47(4H, m), 6.59(1H, d), 7.15(1H, d) ¹³C-NMR (CD₃OD) 34.1, 41.4, 111.2, 122.3, 123.2, 124.8, 128, 133.4, 156.7, 165, 166.5 | HRFABMS Calcd for $C_{11}H_{11}N_5O_2+H^+$: 246.0991: Found: 246.0992 |

According to the present invention, it is possible to economically and efficiently mass produce hymenialdisine and its derivatives by complete chemical synthesis. Further, it is possible to provide intermediates useful for the production of these compounds.

We claim:

1. A process for producing hymenialdisine or its derivatives of the formula (I):

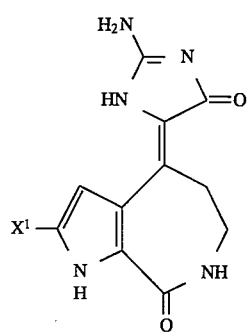

(I)

wherein $X^1$ is a halogen atom or a hydrogen atom, which process comprises reacting a compound having the formula (II):

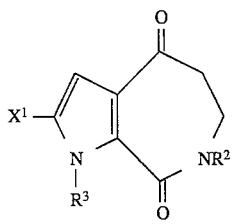
(II)

wherein $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsiloxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxymethyl group, dimethyltexylsiloxymethyl group, or tert-butyldiphenylsiloxymethyl, and $X^1$ is as defined above, with a dialkylphosphoroacetic acid ester having the formula (III):

wherein $R'$ is a substitutable alkyl group having 1 to 4 carbon atoms and $R^1$ is an alky group having 1 to 4 carbon atoms, to synthesize a compound having the formula (IV):

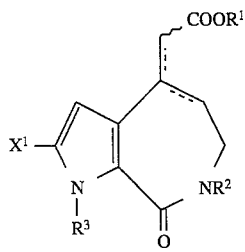
(IV)

wherein $R^1$, $R^2$, $R^3$, and $X^1$ are as defined above, and the dotted line indicates a single bond existing at one or the other position;
reacting the compound having the formula (IV) with an oxidizing agent to synthesize the compound having the formula (V):

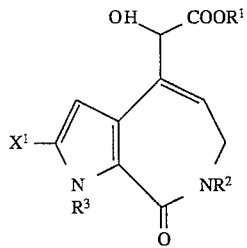
(V)

wherein $R^1$, $R^2$, $R^3$, and $X^1$ are as defined above;
reacting the compound having the formula (V) with a halogenated alkylsulfonyl, halogenated arylsulfonyl, alkyl sulfonyl acid anhydride, or arylsulfonyl acid anhydride to synthesize a compound of the formula (VIa):

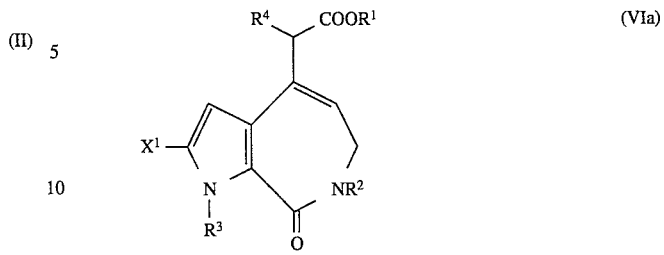
(VIa)

wherein $R^1$, $R^2$, $R^3$, and $X^1$ are as defined above and $R^4$ is an alkylsulfonyloxy group or arylsulfonyloxy group, or reacting a compound having the formula (IVa):

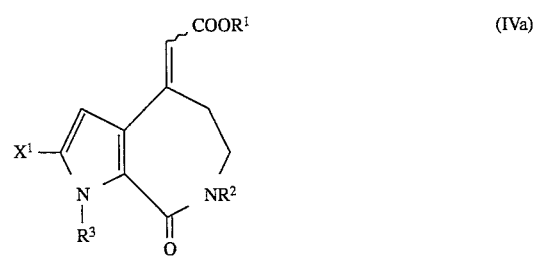
(IVa)

wherein $R^1$, $R^2$, $R^3$, and $X^1$ are as defined above with a halogenating agent to synthesize a compound having the formula (VIb):

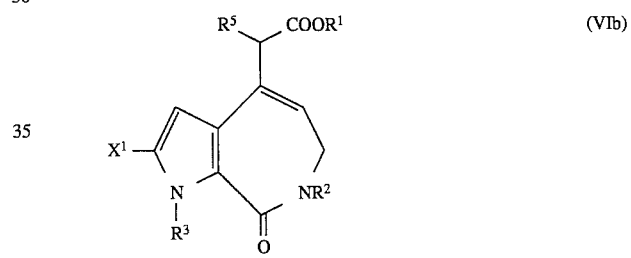
(VIb)

wherein $R^1$, $R^2$, $R^3$, and $X^1$ are as defined above and $R^5$ is a halogen atom; reacting guanidine with a compound having the formula (VIa) or (VIb) to synthesize a compound having the formula (VII):

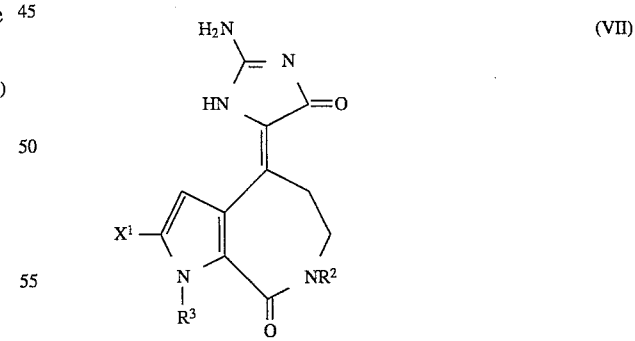
(VII)

wherein $R^2$, $R^3$, and $X^1$ are as defined above;
and deprotecting the compound having the formula (VII).

2. A compound of the formula (IV):

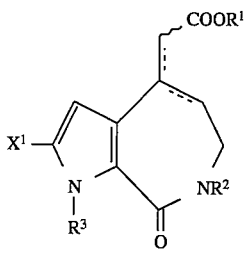

wherein $R^1$ is an alkyl group having 1 to 4 carbon atoms, $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsiloxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxymethyl group, dimethyltexylsiloxymethyl group, or tert-butyldiphenylsiloxymethyl group, $X^1$ is a halogen atom or hydrogen atom, and the dotted lines represent that a single bond is present at either one of the positions.

3. A compound having the formula (VI):

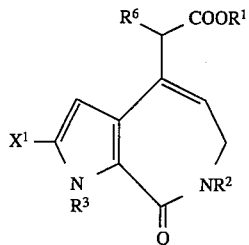

wherein $R^1$ is an alkyl group having 1 to 4 carbon atoms, $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsiloxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxymethyl group, dimethyltexylsiloxymethyl group, or tert-butyldiphenylsiloxymethyl group, $R^6$ is an alkylsulfonyloxy group, arylsulfonyloxy group, or halogen atom, and $X^1$ is a halogen atom or hydrogen atom.

4. A compound of the formula (V):

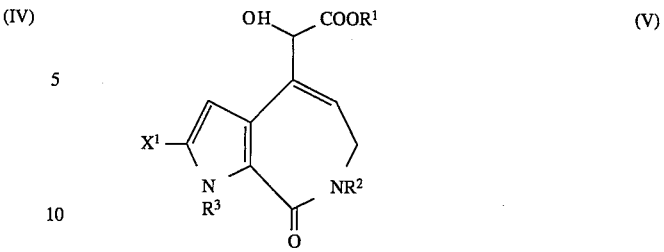

wherein $R^1$ is an alkyl group having 1 to 4 carbon atoms, $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsioxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxymethyl group, dimethyltexylsiloxymethyl group, or tert-butyldiphenylsiloxymethyl group, and $X^1$ is a halogen atom or hydrogen atom.

5. A compound of the formula (VII):

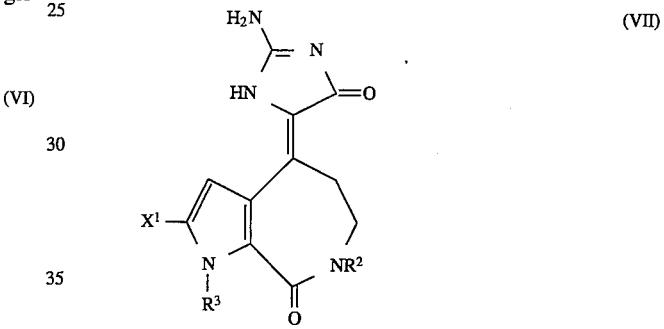

wherein $R^2$ is a trimethylsilylethoxymethyl group, benzyloxymethyl group, p-methoxybenzyloxymethyl group, methoxymethyl group, methoxyethoxymethyl group, tert-butoxymethyl group, p-anisyloxymethyl group, guaiacolmethyl group, tert-butyldimethylsiloxymethyl group, dimethyltexylsiloxymethyl group, or tert-butyldiphenylsiloxymethyl group, $R^3$ is a trimethylsilylethoxymethyl group, benzyloxymethyl group, p-methoxybenzyloxymethyl group, tert-butyldimethylsiloxymethyl group, dimethyltexylsiloxymethyl group, or tert-butyldiphenylsiloxymethyl group, and $X^1$ is a halogen atom or hydrogen atom.

\* \* \* \* \*